United States Patent [19]

Klapp

[11] 4,020,839
[45] May 3, 1977

[54] MEDICAMENT-DISPENSING PACKAGE

[75] Inventor: Steven Michael Klapp, St. Clair Shores, Mich.

[73] Assignee: Parke, Davis & Company, Detroit, Mich.

[22] Filed: Feb. 26, 1976

[21] Appl. No.: 661,664

[52] U.S. Cl. .............................................. 128/272
[51] Int. Cl.² ........................................ A01M 5/34
[58] Field of Search ...................... 128/272–272.3, 128/214 R; 141/329, 330; 222/502, 503, 532

[56] References Cited

UNITED STATES PATENTS

| 532,990 | 1/1895 | Rau ................................... 222/537 |
| 2,953,132 | 9/1960 | Richter et al. ................. 141/329 X |
| 2,957,501 | 10/1960 | Holmes ........................ 128/272.3 X |
| 3,734,360 | 5/1973 | Brown ............................... 222/537 |
| 3,885,607 | 5/1975 | Peltier ........................... 128/272 X |
| 3,938,520 | 2/1976 | Scislowicz et al. ............. 128/272.3 |

Primary Examiner—Allen N. Knowles
Assistant Examiner—Norman L. Stack, Jr.
Attorney, Agent, or Firm—David B. Ehrlinger; George M. Richards; Stephen Raines

[57] ABSTRACT

A medicament-dispensing package for use with a parenteral solution container, including an open-ended transfer tube having a spike at one end and a bi-functional dispensing or loading configuration at the other end, a closure for a medicament container having a transfer chamber rotatably engageable with the loading end of the transfer tube and having means in the form of first and second access openings in the closure and transfer tube, respectively, which can be aligned by rotation for transfer of liquid and/or solid to and from the medicament container by way of the transfer tube.

7 Claims, 3 Drawing Figures

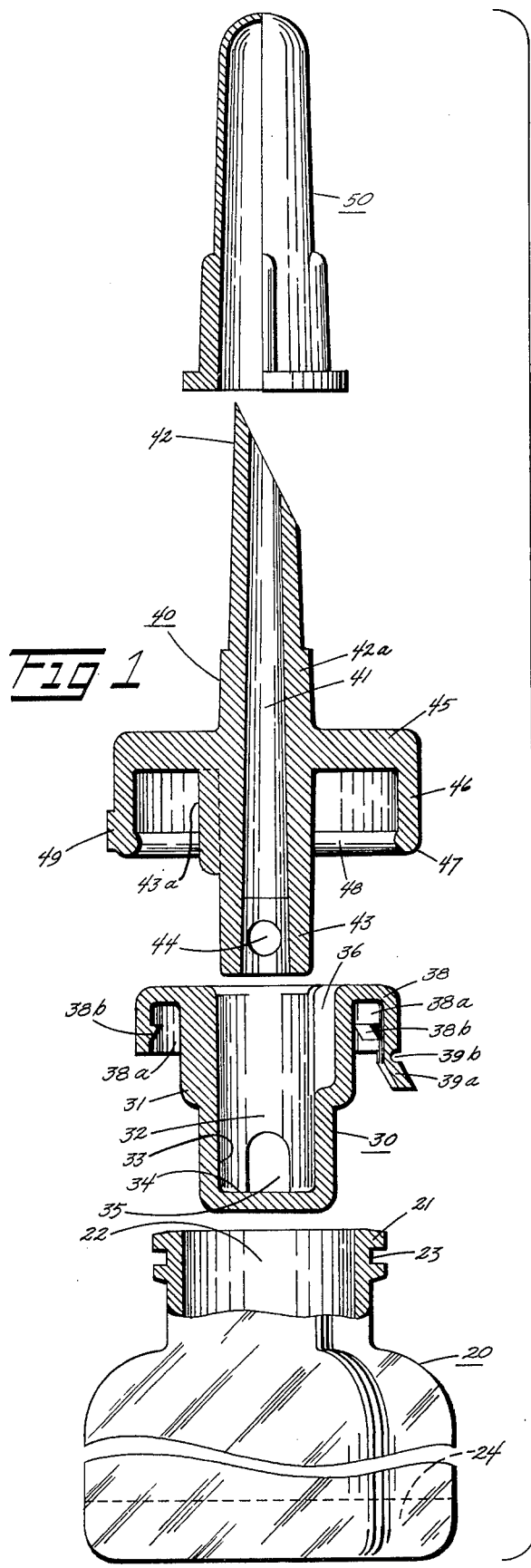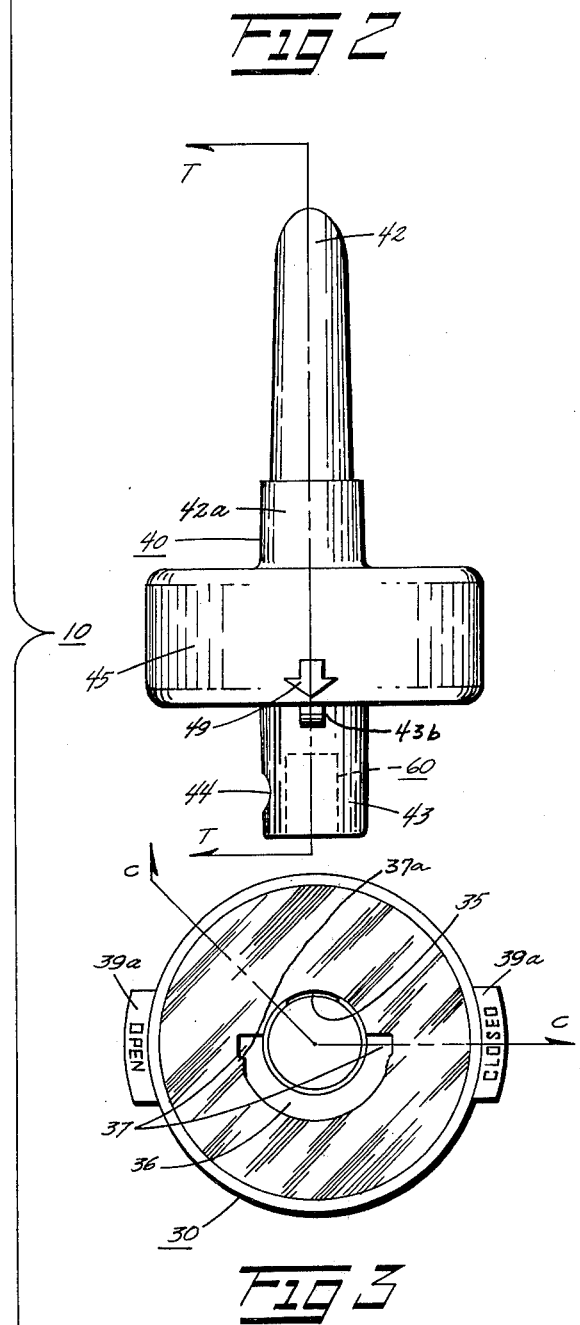

MEDICAMENT-DISPENSING PACKAGE

SUMMARY AND DETAILED DESCRIPTION

This invention relates to a medicament-dispensing package for use with a parenteral solution container and more particularly the invention relates to a package of the kind described providing means for transferring medicament to a parenteral solution container and for dispensing the medicament in solution form from the container by syringe means.

The prior art dispensing packages for medicine for use with parenteral solution containers have used various constructions commonly involving a medicament bottle and closure having a transfer tube with a spike end for puncturing a rubber diaphragm of the parenteral solution container. Use of these devices requires a series of manipulations wherein sterile water is injected through the closure into the bottle containing medicament, a mixture is formed by shaking the contents, the diaphragm of the parenteral solution container is spiked, and the aqueous mixture is transferred to the container to provide the desired final parenteral solution containing medicament accessible by multiple puncturing of the diaphragm with a syringe needle. The difficulty with this procedure is that it unduly exposes the medicament and the sterile water to potential contamination. It also is an inconvenient procedure. Moreover, when unit doses are taken successively from the finished parenteral solution by way of multiple puncturing of the diaphragm, the contents of the solution container are exposed to non-sterile surfaces.

It is therefore an object of the present invention to provide package means for facilitating the dispensing of parenteral medicament solutions.

It is also an object of the invention to provide package means for storing medicament and adapted for eventual engagement with and transfer to separate packaging containing liquid diluent to provide a parenteral solution for dispensing by sterile technic.

These and other objects and advantages will be seen with reference to the accompanying drawing in which:

FIG. 1 is a side view (either in section or part section) of an assembly of components [container, closure (sectioned on line C—C of FIG. 3) and transfer tube and cap (sectioned and half-sectioned, respectively, on line T-T of FIG. 2)] of a preferred form of a medicament-dispensing package;

FIG. 2 is a side view of the transfer tube of the package of FIG. 1 and FIG. 3 is a top view of the closure element of the same package;

Referring to the drawing, FIG. 1 shows a preferred embodiment of a medicament-dispensing package 10 according to the invention including a medicament container 20, a closure 30, a transfer tube 40, and a cap 50 for the transfer tube. The medicament container 20 is a clear bottle or vial provided with a rigid lip 21 defining an axial opening 22. Adjacent to the lip 21 is an annular channel 23 contoured to cooperate with a retention element of a closure member presently to be described.

The closure 30 has a tubular body 31, preferably circular in cross-section, shaped to fit the opening 22 in sealing relation, the outer walls of the body 31 being slightly tapered to facilitate engagement of the closure with the walls of the opening 22 which in turn are conformingly tapered. The closure 30 also has a coaxial transfer chamber 32 defined by side walls 33 which have a slight taper for loading purposes presently to be described. At the bottom 34 of the transfer chamber 32 is an access opening 35 located in the chamber side wall. Adjacent to the transfer chamber 32 is a guide channel 36 in the form of a semi-annulus. At the ends of the channel are diametrically opposed indexing positions 37 for loading and closing purposes, to be described. The closure has a peripheral skirt 38 which is configured to overlie and enclose the lip 21 of the medicament container 20. At the interior of the skirt 38 a channel 38a is provided to fit and accommodate with the lip 21. Circumferentially spaced cleats 38b are also provided in the interior of the skirt 38 for locking purposes to hold the closure in engagement with the medicament container 20. The closure further is provided with diametrically opposed guide flaps 39a, in radial alignment with the indexing positions 37, bearing legends "open" and "closed" to show the relative radial orientation of the transfer tube 40 for loading and sealing purposes respectively.

The transfer tube 40 has a central tapered bore 41. It has a spike 42 at one end adapted for piercing the diaphragm of a parenteral solution bottle. At the other end or loading end 43 it has a generally cylindrical configuration slightly tapered externally to conform with the side walls 33 of the transfer chamber 32. Adjacent to loading end 43 is a circular access opening 44 through the side wall of the tube. The transfer tube is provided with a skirt 45 having an annular side wall 46 which cooperates with the skirt 38 of the closure 30 in covering relation for sealing purposes. The lower edge 47 of the skirt 45 is provided with a retention lip 48 which is contoured to cooperate with a groove 39b located adjacent to each of the guide flaps 39a of the closure 30. The transfer tube 40 also has a peripheral guide lug 43a shaped to fit closely in either of the guide channel indexing portions 37 and to be moved therebetween within the guide channel 36 in a tighter friction fit, for indexing purposes. The lower edge 47 of the skirt carries an alignment indicator or arrow 49 which is in radial alignment with the guide lug 43a. The relative radial orientation of the access openings 35 and 44, arrow 49, and guide flaps 39a is such that the arrow 49 points to the "open" flap 39a when the access openings 35 and 44 are in direct communication and points to the "closed" flap 39a when these openings are diametrically opposed and therefore not in communication. The transfer tube 40 is also provided with a hub 42a which serves as a tapered bearing surface for the cap 50 which is used to cover the spike end 42 of the transfer tube 40. The cap 50 can be removed from the spike end 42 to expose the same and can then be used to cover the loading end 43 of the transfer tube 40 where the diametral configuration is identical to that of the hub 42a.

In a preferred embodiment, the transfer tube 40 is provided with a one-way safety feature or tamper-proof feature which serves to permanently lock the transfer tube in the open position whenever the transfer tube is advanced to that position. This can be accomplished, for example, by providing a squared off trailing edge 43b for the guide lug 43a which catches and locks into a matching relief edge 37a at the indexing position 37.

OPERATION

In operation, the medicament container 20 is loaded with medicament 24 in a form adapted for dissolving in liquid suitable for parenteral administration. The medicament for this purpose may be in any desired form such as liquid, solid, crystalline, amorphous, powdered, freeze-dried, etc. The container is then sealed with the closure 30, being inserted in the opening 22 to the point where the skirt 38 and cleat 38b are in locking engagement with the lip 21 and cleat channel 23 of the container 20. The transfer tube 40 is then inserted with its skirt 45 in covering relation over the closure 30 so that the retention lip 48 coincides with the grooves 39b of the closure. If required, the skirt 45 is rotated to the indexing position where the alignment indicator 49 is pointed at the guide flap 39a bearing the legend "closed". At this setting the access opening 44 is covered in sealing relation by the side wall 33 of the chamber 32 so that the medicament container 20 is effectively sealed off. The cap 50 is then mounted over the spike end 42 of the transfer tube 40 in covering relation. In this sealed form the package can be marketed to the trade for distribution, inventory and sale to the ultimate purchaser with all the benefits of long shelf life, maintenance of sterility, etc. To use the package with a parenteral solution stock container having pierceable diaphragm access, the cap 50 is removed exposing the spike end 42 which is then inserted through the diaphragm. The assembly is then inverted so that some of the liquid is available to pass through the bore 41 of the transfer tube. At the same time the transfer tube 40 is rotated half-way (180°) with respect to the closure 30 so that the alignment indicator 49 is moved from the "closed" position to the "open" position. In the later position the access opening 44 is brought into alignment with the access opening 35 of the closure so that there is open communication between the bore 41 and the interior of the medicament container 20. As a result the parenteral solution is able to pass by gravity flow into the latter container in controlled fashion where it can be mixed with and used to dissolve the medicament content 24 of the container. The invention also contemplates a construction wherein the element 37a is gradually inclined rather than squared off so that, if desired, while carrying out the dissolution of the medicament the transfer tube can be rotated away from the open position so that the open communication between the stock container and the medicament container is temporarily broken off. In other words, the transfer tube can be used as a valve for purposes of manipulatiion so that the amount of liquid introduced to the medicament container can be precisely controlled for purposes of dissolving the medicament.

Finally, when the dissolving of the medicament has reached completion, as may be noted by visual inspection, the assembly is again inverted and the indicator 49 is set in the open position allowing the medicament to flow by gravity back to the parenteral solution stock container where it is mixed by shaking to assure thorough distribution of the medicament with the parenteral solution. The assembly can for this purpose be inverted several times.

When the mixture is complete the transfer tube is then disconnected from the closure 30 and the latter, together with the original medicament container 20, can be discarded. The transfer tube 40 can then be sealed with the cap 50 at its loading end 41 so that the open end thereof is covered as well as the access opening 44, for sterility purposes. The container sealed in this way can be held indefinitely until needed. When it is desired to administer the medicament solution by syringe means, the container is uncapped and the hub (60, FIG. 2, dotted outline) of a syringe is inserted into the open bore 41. The bore, as a feature of the invention, has a Luer-taper to receive the hub in closely matching leakproof fit. The syringe with the parenteral solution stock container inverted is then filled as desired, then withdrawn, and the syringe used in conventional fashion for parenteral administration of the medicament solution. The dispensng process can then be repeated as frequently as desired advantageously will full control and with assurance that the apparatus and technic are maintained sterile.

While the invention has been set forth in considerable detail, it will be realized that the invention is subject to considerable variation in such detail without departing from the scope of the invention as hereinafter claimed.

I claim:

1. A medicament-dispensing package for use with a parenteral solution container comprising
    a medicament container having an open mouth,
    a closure including a skirt in locking engagement with said container, the closure being in sealing relation with the mouth and including an axial recessed tubular transfer chamber having a distal end extending within said mouth in the sealing relation, the distal end having a first off-center access opening communicating with the interior of the medicament chamber,
    and an open-ended transfer tube having a spike end and an opposite loading end, the loading end having a second off-center access opening and being joinable in telescopic relation with the transfer chamber and rotatable therewith in joined relation to and from a dispensing position in which said first and second access openings are in alignment for transfer of liquid and/or solid to and from the container by way of transfer tube, the transfer tube being detachable in telescopic relation from the transfer chamber such that after dispensing contents of said medicament container to a parenteral solution container by means of the spike end, the transfer tube can be telescopically disconnected from the closure.

2. A medicament-dispensing package according to claim 1 in which the bore of the loading end of the transfer tube has a taper to accommodate a syringe hub.

3. A medicament-dispensing package according to claim 1 including a protective cap adapted to cover either of the loading and spike ends of the transfer tube interchangeably.

4. A medicament-dispensing package according to claim 1 comprising a cap for the closure integral with the transfer tube, said cap including a skirt removably engageable in covering relation with the closure skirt.

5. A medicament-dispensing package according to claim 1 having lug and channel means for indexing the rotation to the dispensing position.

6. A medicament-dispensing package according to claim 5 which includes detent means for locking the transfer tube in the dispensing position.

7. A medicament-dispensing package according to claim 5 which includes detent means for permanently locking the transfer tube in the dispensing position.

* * * * *

UNITED STATES PATENT AND TRADEMARK OFFICE
CERTIFICATE OF CORRECTION

PATENT NO. : 4,020,839
DATED : May 3, 1977
INVENTOR(S) : Steven Michael Klapp

It is certified that error appears in the above-identified patent and that said Letters Patent are hereby corrected as shown below:

Column 3, line 64, delete "41" and insert:

--42--.

Column 4, line 11, delete "will" and insert in its place:

--with--.

Signed and Sealed this twenty-third Day of August 1977

[SEAL]

Attest:

RUTH C. MASON
*Attesting Officer*

C. MARSHALL DANN
*Commissioner of Patents and Trademarks*